United States Patent [19]
Adams

[11] Patent Number: 5,994,504
[45] Date of Patent: Nov. 30, 1999

[54] VITAMIN D RESPONSE ELEMENT BINDING PROTEIN

[75] Inventor: John S. Adams, Los Angeles, Calif.

[73] Assignee: Cedars-Sinai Medical Center, Los Angeles, Calif.

[21] Appl. No.: 08/799,429

[22] Filed: Feb. 12, 1997

Related U.S. Application Data

[60] Provisional application No. 60/011,612, Feb. 12, 1996.

[51] Int. Cl.$^6$ .............................. C07K 4/12; C07K 14/47
[52] U.S. Cl. ........................... 530/350; 530/300; 514/12; 435/69.1
[58] Field of Search ................................... 530/350, 300; 514/12; 435/69.1

[56] References Cited

U.S. PATENT DOCUMENTS

| | | |
|---|---|---|
| 4,816,567 | 3/1989 | Cabilly et al. . |
| 5,064,770 | 11/1991 | DeLuca et al. . |

FOREIGN PATENT DOCUMENTS

| | | |
|---|---|---|
| WO89/02922 | 6/1989 | WIPO . |

OTHER PUBLICATIONS

Adelman et al., "In vitro deletional mutagenesis for bacterial production of the 20,000–Dalton form of human pituitary growth hormone," *DNA* 2:183–193 (1983).
Arbelle et al., "Inhibition of vitamin D receptor–retinoid X receptor–vitamin D response element complex formation by nuclear extracts of vitamin D–resistant new world primate cells," *Endocrinology* 137:786–789 (1996).
Ausubel et al., *Current Protocols in Molecular Biology* John Wiley & Sons vol. 1 (1995) pp. 1 & 2.
Brandon et al., "Glucocorticoid resistance in humans and nonhuman primates," *Cancer Res.* 49:2203–2213 (1989).
Chrousos et al., "Uterine estrogen and progesterone receptors in an estrogen– and progesterone– "resistant" primate," *J. Clin. Endocrinol. Metab.* 58:516–520 (1984).
Chrousos et al., "Adaptation of the mineralocorticoid target tissues to the high circulating cortisol and progesterone plasma levels in the sqirrel monkey," *Endocrinol.* 115:25–32 (1984).
Crea et al., "Chemical synthesis of genes for human insulin," *Proc. Natl. Acad. Sci. USA* 75:5765–5769 (1978).
Cunningham and Wells, "High–resolution epitope mapping of hGH–receptor interactions by alanine–scanning mutagenesis," *Science* 224:1081–1085 (1989).
Gacad and Adams, "Identification of a competitive binding component in vitamin D–resistant new world primate cells with a low affinity but high capacity for 1,25–dihydroxyvitamin $D_3$" *J. Bone Min. Res.* 8:27–35 (1993).
Goding et al., Monoclonal Antibodies: Principles and Practice pp. 59–103 Academic Press, Inc., San Diego (1986).
Goeddel et al., Gene Expression Technology: Methods in Enzymology vol. 185 Academic Press, Inc., San Diego (1991) pp. 1 & 2.
Houghten et al., "Generation and use of synthetic peptide combinatorial libraries for basic research and drug discovery" *Nature* 354:84–86 (1991).
Kaplit and Lowrey, *iral Vector Gene Therapy and Neuroscience Applications,* Academic Press, San Diego (1995) (pp. V–XVII).
Lam et al., "A new type of synthetic peptide library for identifying ligand–binding activity" *Nature* 354:82–84 (1991).
Lipsett et al., "The defective glucocorticoid receptor in man and nonhuman primates," *Recent Prog. Hormone Res.* 41:199–246 (1985).
Ozono et al., "The vitamin D–responsive element in the human osteocalcin gene" *J. Biol. Chem.* 265:21881–21888 (1990).
Roth ed. *Protein Expression in Animal Cells,* Academic Press, San Diego vol. 43 (1994) pp. 1 & 2.
Sambrook et al., *Molecular Cloning: A Laboratory Manual* 2nd edition, Cold Spring Harbor Press (1989) pp. 1 & 2.
Songyang et al., "SH2 domains recognize specific phosphopeptide sequences" *Cell* 72:767–778 (1993).
Takahashi et al.., "The mechanism of end–organ resistance to 1α, 25–dihydroxycholecalciferol in the common marmoset" *Biochem S.* 227:555–563 (1985).
Veira et al., "Production of single–stranded plasmid DNA," *Meth. Enzymol.* 153:3–11 (1987).
Zoller and Smith, "Oligonucleotide–directed mutagenesis using M13–derived vectors: an efficient and general procedure for the production of point mutations in any fragment of DNA," *Nucleic Acids Res.* 10:6487–6500 (1982).
Arbelle et al Clin Research vol. 41 (2) Abstract 238A, 1993.
Haussler et al Bone vol. 17(2) Supplement 335–385, Aug. 1995.
Arbelle et al Endocrinology vol. 137(2) 786–788, 1996.

*Primary Examiner*—Julie Burke
*Attorney, Agent, or Firm*—Campbell & Flores LLP

[57] ABSTRACT

The invention relates to the discovery and purification of novel vitamin D response element binding proteins and the isolation of polynucleotide sequences encoding the proteins. Vitamin D response element binding proteins are distinct from the vitamin D receptor. Vitamin D response element binding proteins can interfere with the biological activity of the vitamin D receptor and other related intracellular receptor proteins. One aspect of the invention is to provide purified vitamin D response element binding proteins. Another aspect of the invention is to provide polynucleotides encoding the vitamin D response element binding proteins of the invention and to provide polynucleotides complementary to polynucleotide coding strand. Another aspect of the invention is to provide antibodies capable of binding to the vitamin D response element binding proteins of the invention. Another aspect of the invention is to provide assays for the detection or screening of therapeutic compounds that interfere with the interaction between vitamin D response element binding protein and vitamin D response elements.

8 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:1:

GGTTCACGAG GTTCA                                                      15

(2) INFORMATION FOR SEQ ID NO:2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:2:

GGGTGAACGG GGGCA                                                      15

(2) INFORMATION FOR SEQ ID NO:3:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:3:

AGGTCACAGT GACCT                                                      15

(2) INFORMATION FOR SEQ ID NO:4:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:4:

AGAACATCCT GTTCT                                                      15

(2) INFORMATION FOR SEQ ID NO:5:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:5:

Ser Arg Ser Gly Gly Gly Gly Gly Gly Ile Gly Ser Gly Gly Ser
 1               5                  10                  15

Leu Arg

-continued (2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

```
Phe Tyr Leu Pro Xaa Glu Ile Xaa Asp Tyr Gly Gln Asp Glu Glu Ala
1               5                   10                  15
Val Lys
```

VITAMIN D RESPONSE ELEMENT BINDING PROTEIN

This application claims priority to U.S. provisional application Ser. No. 60/011,612, filed Feb. 12, 1996.

Portions of the invention described herein were made in the course of research supported in part by NIH grants DK33139 and DK09093. The Government may have certain rights in this invention.

1.0. FIELD OF THE INVENTION

The invention is in the field of vitamin D cellular signaling.

2.0. BACKGROUND

Most genera of new world primates exhibit vitamin D resistance, i.e., insensitivity that may be characterized biochemically by the maintenance of high circulating concentration of the active vitamin D metabolite 1,25 dihydroxy vitamin D3, Gacad et al J. Bone Min. Res. 8:27–35 (1993). Humans and old world primates, on the other hand, do not exhibit vitamin D resistance. This vitamin D resistance phenomenon in new world primates is also correlated with high circulating levels of other steroid hormones including glucocorticoid (Chrousos et al *Endocrinology* 115:25–32 (1984), Lipsett et al *Recent Prog. Hormone Res.* 42:199–246 (1985), Brandon et al *Cancer Res.* 49:2203–2213 (1989)), mineral corticoid, progesterone, testosterone, 17β-estradiol (Chrousos et al *J. Clin. Endocrinol. Metab.* 58:516–920 (1984)), 1,25-$(OH)_2D$ (Takahashi et al *Biochem S.* 227:555–563 (1985)).

By gaining an understanding of the biochemical mechanisms behind vitamin D resistance and the high levels of circulating steroid hormones in new world primates, new opportunities for treating and diagnosing diseases related to either over-production or under-production of vitamin D and other steroidal hormones may be achieved. Such diseases include osteoporosis, hypercalcemia, and vitamin D intoxication, hypersecretion of steroid hormones, and the like.

Vitamin D receptors bind to the consensus vitamin D response element as described in Ozono et al *J. Biol Chem.* 265:21881–21888 (1990). The invention described herein relates to the discovery of a novel protein that inhibits that binding of vitamin D receptor to vitamin D receptor binding element. By inhibiting the binding of the vitamin D receptor to vitamin D response elements, it is possible to modulate the expression of genes regulated by estrogen via vitamin D receptors. Vitamin D and vitamin D receptors play a significant role in the etiology of many diseases such as osteoporosis and some cancers, e.g. tumors that include hypercalcemia. It is thus of interest to provide proteins that interact with vitamin D response elements and polynucleotides encoding such proteins.

3.0. SUMMARY OF THE INVENTION

The invention relates to the discovery and purification of novel vitamin D response element binding proteins and the isolation of polynucleotide sequences encoding the proteins. Vitamin D response element binding proteins are of interest because they may mediate the high levels steroid hormones observed in new world primates. Vitamin D response element binding proteins are distinct from the vitamin D receptor. Vitamin D response element binding proteins can interfere with the biological activity of the vitamin D receptor and other related intracellular receptor proteins. Vitamin D response element binding proteins of the invention can bind to a DNA sequence known as the vitamin D response element that is conserved (or partially conserved) among the regulatory regions of estrogen regulated genes. By binding to vitamin D response elements, vitamin D response element binding proteins may prevent binding to the element by vitamin D receptors. These properties of vitamin D response element binding proteins have profound physiological effects. Thus by regulating the intracellular levels of the subject vitamin D response element binding proteins, desirable physiological effects may be obtained. Such effects may be used to treat a variety of diseases involving the signaling at intracellular receptors including osteoporosis, glucocorticoid mediated disorders, hypercalcemia associated with vitamin D over-production, and various granuloma forming diseases.

One aspect of the invention is to provide purified vitamin D response element binding proteins. The purified proteins may be obtained from either recombinant cells or naturally occurring cells. The purified vitamin D response element binding proteins of the invention may be mammalian in origin. Primate, including human and *Callithrix jacchus* (common marmoset), derived vitamin D response element binding proteins are examples of the various vitamin D response element binding proteins specifically provided for. The invention also provides allelic variants and biologically active derivatives of naturally occurring vitamin D response element binding proteins.

Another aspect of the invention is to provide polynucleotides encoding the vitamin D response element binding proteins of the invention and to provide polynucleotides complementary to polynucleotide coding strand. The polynucleotides of the invention may be used to provide for the recombinant expression of vitamin D response element binding proteins. The polynucleotides of the invention may also be used for genetic therapy purposes so as to treat diseases related to vitamin D receptors and ligands that bind to vitamin D receptors. The invention also provides polynucleotides for use as hybridization probes and amplification primers for the detection of naturally occurring polynucleotides encoding vitamin D response element binding proteins.

The invention also provides for single or double-stranded oligonucleotides that mimic sterol response elements and are consequently capable of binding sterol receptors (e.g., the VDR), or sterol response element binding proteins (e.g., VDRE—BP). Such oligonucleotides are generally chemically synthesized, and preferably comprise a nuclease resistant back-bone. Optionally, the oligonucleotides are chemically modified to reduce the net charge of the molecules in order to increase solubility across the cell membrane.

Another aspect of the invention is to provide antibodies capable of binding to the vitamin D response element binding proteins of the invention. The antibodies may be polyclonal or monoclonal. The invention also provides methods of using the subject antibodies to detect and measure expression of vitamin D response element binding protein either in vitro or in vivo.

Another aspect of the invention is to provide assays for the detection or screening of therapeutic compounds that interfere with the interaction between vitamin D response element binding protein and vitamin D response elements. The assays of the invention comprise the step of measuring the effect of a compound of interest on binding between vitamin D response element binding protein and an vitamin D response element. Binding may be measured in a variety of ways, including the use of labeled vitamin D response element binding protein or labeled DNA sequences comprising an vitamin D response binding element.

4.0. DESCRIPTION OF THE SPECIFIC EMBODIMENTS

The invention relates to the discovery and purification of novel vitamin D response element binding proteins and the isolation of polynucleotide sequences encoding the proteins. Vitamin D response element binding proteins are of interest because, among other reasons, they modulate the activity of vitamin D receptors. Vitamin D response element binding proteins are distinct from the vitamin D receptor. Vitamin D response element binding proteins can interfere with the activity of the vitamin D receptor by binding to the same DNA sequence, i.e., the vitamin D receptor binding element. Thus by regulating the intracellular levels of the subject vitamin D response element binding proteins, physiological effects of interest may be obtained. Such effects may be used to treat a variety of diseases involving the signaling at intracellular receptors including osteoporosis, glucocorticoid mediated disorders, hypercalcemia associated with vitamin D over-production, and granuloma forming diseases.

The term "Vitamin D" is used broadly herein. Unless noted otherwise, the term "Vitamin D" includes both the natural mammal-derived form of vitamin D (vitamin D3, cholecalciferol), the plant-derived form of vitamin D (vitamin D2, ergocalciferol) and various metabolites of vitamin D such as 25-hydroxy vitamin D (25 [OH] D), 1,25 dihydroxy vitamin D (1,25 [OH]$_2$D), 25,26-dihydroxy vitamin D (25,26 [OH]$_2$D), and the like.

The vitamin D response element binding proteins of the invention have the biological activity of specifically binding to vitamin D response element DNA sequences, including the vitamin D response element consensus sequence and vitamin D response elements from one or more genes.

The vitamin D response element binding proteins of the invention may be isolated from a variety of mammalian animal species. Preferred mammalian species for isolation are primates, humans and new world primates being particularly preferred. Although humans and old world primates do not produce large enough quantities of vitamin D response element binding protein to manifest the Vitamin D resistance phenomenon seen in new world primates, humans and old world primates (as well as other mammals) are believed to produce vitamin D response element binding proteins. The invention also contemplates allelic variants of vitamin D response element binding protein. Vitamin D response element binding proteins may be prepared from a variety of mammalian tissues, however leukocytes and cell lines established from blood leukocytes are preferred non-recombinant sources of vitamin D response element binding proteins. Preferably vitamin D response element binding proteins are obtained from recombinant host cells genetically engineered to express significant quantities of vitamin D response element binding proteins. Vitamin D response element binding proteins may be isolated from non-recombinant cells in a variety of ways well known to a person of ordinary skill in the art. One example of such an isolation method is provided below in the example section. Methods for purifying recombinant proteins from genetically engineered host cells vary with the host cell type and are well known to persons of ordinary skill in the art.

The term "vitamin D response element binding protein" as used herein refers not only to proteins having the amino acid residue sequence of naturally occurring vitamin D response element binding proteins but also refers to functional derivatives and variants of naturally occurring vitamin D response element binding protein. A "functional derivative" of a native polypeptide is a compound having a qualitative biological activity in common with the native polypeptide. Thus, a functional derivative of a native vitamin D response element binding protein is a compound that has a qualitative biological activity in common with a native vitamin D response element binding protein, e.g., binding to vitamin D3 and other cognate ligands. "Functional derivatives" include, but are not limited to, fragments of native polypeptides from any animal species (including humans), and derivatives of native (human and non-human) polypeptides and their fragments, provided that they have a biological activity in common with a respective native polypeptide. "Fragments" comprise regions within the sequence of a mature native polypeptide. The term "derivative" is used to define amino acid sequence and glycosylation variants, and covalent modifications of a native polypeptide, whereas the term "variant" refers to amino acid sequence and glycosylation variants within this definition. Preferably, the functional derivatives are polypeptides which have at least about 65% amino acid sequence identity, more preferably about 75% amino acid sequence identify, even more preferably at least 85% amino acid sequence identity, most preferably at least about 95% amino acid sequence identity with the sequence of a corresponding native polypeptide. Most preferably, the functional derivatives of a native vitamin D response element binding protein retain or mimic the region or regions within the native polypeptide sequence that directly participate in ligand binding. The phrase "functional derivative" specifically includes peptides and small organic molecules having a qualitative biological activity in common with a native vitamin D response element binding protein.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

Amino acid sequence variants of native vitamin D response element binding proteins and vitamin D response element binding protein fragments are prepared by methods known in the art by introducing appropriate nucleotide changes into a native or variant vitamin D response element binding protein encoding DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the vitamin D response element binding protein, the amino acid sequence variants of vitamin D response element protein are preferably constructed by mutating the DNA, either to arrive at an allele or an amino acid sequence variant that does not occur in nature.

Alternatively or in addition, amino acid alterations can be made at sites that differ in vitamin D response element binding proteins from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" Cunningham and Wells, *Science* 244, 1081–1085 (1989). Here, a residue or group of target resides is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding an vitamin D response element binding protein variant can, for example, be obtained by chemical synthesis.

More preferably, DNA encoding an vitamin D response element binding protein amino acid sequence variant is prepared by site-directed mutagenesis of DNA that encodes an earlier prepared variant or a nonvariant version of the vitamin D response element binding protein. Site-directed (site-specific) mutagenesis allows the production of vitamin D response element binding protein variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2:183 (1983). As will be appreciated, the site-specific mutagenesis technique typically employs a phage vector that exists in both a single-stranded and double-stranded form. Typical vectors useful in site-directed mutagenesis include vectors such as the M13 phage. This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication, Veira et al., *Meth. Enzymol.* 153:3 (1987)] may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis may be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desires mutation. This heteroduplex vector is then used to transform appropriate host cells such as HB101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of an vitamin D response element binding protein. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primes can be easily sequenced. PCR amplification using a primer pair like the one just described results in a population of DNA fragments that differ at the position of the mutation specified by the primer, and possibly at other positions, as template copying is somewhat error-prone.

Further details of the foregoing and similar mutagenesis techniques are found in general textbooks, such as, for example, Sambrook et al., *Molecular Cloning: H Laboratory Manual 2nd edition*, Cold Spring Harbor Press, Cold Spring Harbor (1989), and *Current Protocols in Molecular Biology*, Ausubel et al. eds., John Wiley and Sons (1995).

Naturally-occurring amino acids are divided into groups based on common side chain properties:
  (1) hydrophobic: norleucine, met, ala, val, leu, ile;
  (2) neutral hydrophobic: cys, ser, thr;
  (3) acidic: asp, glu;
  (4) basic: asn, gln, his, lys, arg;
  (5) residues that influence chain orientation: gly, pro; and
  (6) aromatic: trp, tyr, phe.

Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant, and may result in vitamin D response element binding protein variants which block vitamin D response element binding protein biological activities, i.e., binding to vitamin D response elements. Amino acid positions that are conserved among various species are generally substituted in a relatively conservative manner if the goal is to retain biological function.

Amino acid sequence deletions generally range from about 1 to 30 residues, more preferably about 1 to 10 residues, and typically are contiguous. Deletions may be introduced into regions not directly involved in ligand binding.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the vitamin D response element binding protein amino acid sequence) may range generally from about 1 to 10 residues, more preferably 1 to 5 residues, more preferably 1 to 3 residues. Examples of terminal insertions include the vitamin D response element binding proteins with an N-terminal methionyl residue, an artifact of direct expression in bacterial recombinant cell culture, and fusion of a heterologous N-terminal signal sequence to the N-terminus of the vitamin D response element binding protein to facilitate the secretion of the mature vitamin D response element binding protein from recombinant host cells. Such signal sequences will generally be obtained from, and thus homologous to, the intended host cell species. Suitable sequences include STII or Ipp for *E. coli,* alpha factor for yeast, and viral signals such as herpes gD for mammalian cells. Other insertional variants of the native vitamin D response element binding protein molecules include the fusion of the N- or C-terminus of an vitamin D response element binding protein to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in PCT published application WO 89/02922.

Since it is often difficult to predict in advance the characteristics of a variant vitamin D response element binding protein, it will be appreciated that screening will be needed to select the optimum variant. For this purpose biochemical screening assays, such as those described hereinbelow, will be readily available.

The invention also provides for isolated polynucleotides that encode vitamin D response element binding proteins. The polynucleotides provided for may encode complete vitamin D response element binding proteins or portions thereof. The polynucleotides of the invention may be produced by a variety of methods including in vitro chemical synthesis using well known solid phase synthesis technique, by cloning or combinations thereof. The polynucleotides of the invention may be single stranded or double stranded. The polynucleotide of the invention may be derived from cDNA or genomic libraries. Persons of ordinary skill in the art are familiar with the degeneracy of the genetic code and may readily design polynucleotides that encode vitamin D response element binding proteins that have either partial or polynucleotide sequence homology to naturally occurring polynucleotide sequences encoding vitamin D response element binding proteins. The polynucleotides of the invention may be single stranded or double stranded. Polynucleotide complementary to polynucleotides encoding vitamin D response element binding proteins are also provided.

Polynulceotides encoding an vitamin D response element binding protein can be obtained from CDNA libraries prepared from tissue believed to possess vitamin D response element binding protein mRNA and to express it at a detectable level. For example, cDNA library can be constructed by obtaining polyadenylated mRNA from a cell line known to express vitamin D response element binding protein, and using the mRNA as a template to synthesize double stranded cDNA. Alternatively, DNA encoding vitamin D response element binding proteins can be obtained from cDNA libraries prepared from tissue know to express a previously identified vitamin D response element binding proteins at a detectable level. The vitamin D response element binding protein genes can also be obtained from a genomic library, such as a human genomic cosmid library.

Libraries, either cDNA or genomic, are screened with probes designed to identify the gene of interest or the protein encoded by it. For cDNA expression libraries, suitable probes include monoclonal and polyclonal antibodies that recognize and specifically bind to an vitamin D response element binding protein. For cDNA libraries, suitable probes include carefully selected oligonucleotide probes (usually of about 20–80 bases in length) that encode known or suspected portions of an vitamin D response element binding protein from the same or different species, and/or complementary or homologous cDNAs or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual,* New York, Cold Spring Harbor Laboratory Press, 1989).

A preferred method of practicing this invention is to use carefully selected oligonucleotide sequences to screen cDNA libraries from various tissues. The oligonucleotide sequences selected as probes should be sufficient in length and sufficiently unambiguous that false positives are minimized. The actual nucleotide sequence(s) is/are usually designed based on regions of an vitamin D response element binding protein that have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\tau^{32}P$) and polynucleotide kinase to radiolabel the 5' end of the oligonucleotide. However, other methods may be used to label the oligonucleotide, including, but not limited to, biotinylation or enzyme labeling.

cDNAs encoding vitamin D response element binding proteins can also be identified and isolated by other known techniques of recombinant DNA technology, such as by direct expression cloning or by using the polymerase chain reaction (PCR) as described in U.S. Pat. No. 4,683,195, in section 14 of Sambrook, et al., *Molecular Cloning: A Laboratory Manual,* second edition, Cold Spring Harbor Laboratory Press, New York, 1989, or in Chapter 15 of *Current Protocols in Molecular Biology,* Ausubel et al. eds., Green Publishing Associates and Wiley-Interscience 1991. This method requires the use of oligonucleotide probes that will hybridize to DNA encoding an vitamin D response element binding protein.

The polynucleotides of the invention have a variety of uses the particular uses for a given polynucleotide depend, in part, on the specific polynucleotide embodiment of interest. The polynucleotides of the invention may be used as hybridization probes to recover vitamin D response element binding proteins from genetic libraries. The polynucleotides of the invention may also be used as primers for the amplification of vitamin D response element binding protein encoding polynucleotides or a portion thereof through the polymerase chain reaction (PCR) and other similar amplification procedures. The polynucleotides of the invention may also be used as probes and amplification primers to detect mutations in vitamin D response element binding protein encoding genes that have been correlated with diseases, particularly diseases related to overexpression or underexpression of ligands for vitamin D response element binding protein.

The invention also provides a variety of polynucleotide expression vectors comprising the vitamin D response element binding proteins of the invention. The subject expression vectors comprise a polynucleotide sequence encoding an vitamin D response element binding protein in functional combination with one or more promoter sequences so as to provide for the expression of the vitamin D response element binding protein (or an anti-sense copy of the sequence suitable for inhibition of expression of an endogenous gene). The vectors may comprise additional polynucleotide sequences for gene expression, regulation, or the convenient manipulation of the vector, such additional sequences include terminators, enhancers, selective markers, packaging sites, and the like. Detailed description of polynucleotide expression vectors and their use can be found in, among other places *Gene Expression Technology: Methods in Enzymology Volume* 185 Goeddel ed, Academic Press Inc., San Diego, Calif. (1991), *Protein Expression in Animal Cells* Roth ed., Academic Press, San Diego, Calif. (1994).

The polynucleotide expression vectors of the invention have a variety of uses. Such uses include the genetic engineering of host cells to express vitamin D response element binding proteins. The polynucleotide expression vectors of the invention may also be used for genetic therapy for diseases and conditions in which it may be desirable use to express vitamin D response element binding proteins at levels greater than naturally occurring expression levels. Alternatively, it may be desirable to the subject vectors for anti-sense expression to reduce the naturally occurring levels of vitamin D response element binding protein.

The subject invention also provides a general assay and method for screening for molecules that effect the interaction of the VDR with the VDRE. Using the VDR—VDRE (or VDRE—BP—VDRE) interaction in an electromobility shift assay (EMSA) to screen for the presence of such a factor, any of a wide variety of compounds could be screened for the ability to disrupt or enhance the VDR-mediated cellular activity.

The compounds that may be screened in accordance with the invention include but are not limited to peptides, antibodies and fragments thereof, and other organic compounds (e.g., peptidomimetics) that bind to the VDR or the VDRE and either mimic the activity triggered by the natural ligand (i.e., agonists) or inhibit the activity triggered by the natural ligand (i.e., antagonists); as well as peptides, antibodies or fragments thereof, and other organic compounds that mimic the VDRE—BP or the VDRE (or a portion thereof) and effectively "neutralize" the VDR.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are preferably able to cross the blood-brain barrier, gain entry into an appropriate brain cell (e.g. pituitary cell, etc.) and affect the regulation of steroid hormone or vitamin D levels in the body.

The subject invention provides methods for the treatment of a variety of diseases characterized by undesirably high levels of estrogen or other steroids that can bind to vitamin D response element binding proteins of the invention. Diseases may be treated through either in vivo or in vitro genetic therapy. Protocols for genetic therapy through the use of viral vectors can be found, among other places, in *Viral Vector Gene Therapy and Neuroscience Applications,* Kaplit and Lowry, Academic Press, San Diego (1995). The genetic therapy methods of the invention comprise the step of introducing a vector for the expression of vitamin D response element binding protein (or inhibitory anti-sense RNA) into a patient cell. The patient cell may be either in the patient, i.e., in vivo genetic therapy, or external to the patient and subsequently reintroduced into the patient, i.e., in vitro genetic therapy. Diseases that may be treated by the subject genetic therapy methods include osteoporosis, vitamin D toxicity, glucocorticoid hormone overproduction, sex steroid hormone overexpression and underexpression, hypercalcemia (attributable to vitamin D overexpression), granuloma forming diseases and the like.

Another aspect of the invention is to provide assays useful for determining if a compound of interest can bind to vitamin D response element binding proteins so as to interfere with the binding of an vitamin D response element to vitamin D response element receptor proteins. The assay comprises the steps of measuring the binding of a compound of interest to an vitamin D response element binding protein. Either the intracellular binding protein or the compound of interest to be assayed may be labeled with a detectable label, e.g., a radioactive or fluorescent label, so as to provide for the detection of complex formation between the compound of interest and the vitamin D response element binding protein. In another embodiment of the subject assays, the assays involve measuring the interference, i.e., competitive binding, of a compound of interest with the binding interaction between an vitamin D response element binding protein and an vitamin D response element. For example, the effect of increasing quantities of a compound of interest on the formation of complexes between radioactivity labeled vitamin D2 and an vitamin D response element binding protein may be measured by quantifying the formation of labeled ligand-vitamin D response element binding protein complex formation. Additional residue in measuring ligand binding to vitamin D response element binding proteins can be found in the example section below.

Polyclonal antibodies to vitamin D response element binding proteins generally are raised in animals by multiple subcutaneous (sc) or intraperitoneal (ip) injections of an vitamin D response element binding protein and an adjuvant. It may be useful to conjugate a vitamin D response element binding protein or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine resides), glutaraldehyde, succinic anhydride, $SOCl_2$, or $R_1N=C=NR$, where R and $R_1$ are different alkyl groups.

Animals are immunized against the immunogenic conjugates or derivatives by combing 1 mg or 1 μg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant by subcutaneous injection at multiple sites. 7 to 14 days later the animals are bled and the serum is assayed for anti-vitamin D response element binding proteins antibody titer. Animals are boosted until the titer plateaus. Preferably, the animal boosted with the conjugate of the same vitamin D response element binding protein, but conjugated to a different protein and/or through a different cross-linking reagent. Conjugates also can be made in recombinant cell culture as protein fusions. Also, aggregating agents such a alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, the anti-vitamin D response element binding protein monoclonal antibodies of the invention may be made using the hybridoma method first described by Kohler & Milstein, Nature 256:495 (1975), or may be made by recombinant DNA methods [Cabilly, et al, U.S. Pat. No. 4,816,567].

In the hybridoma method, a mouse or other appropriate host animal, such a hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell, see Goding, *Monoclonal Antibodies: Principles and Practice*, pp.59–103 (Academic Press, San Diego (1986).

The anti-vitamin D response element binding protein specific antibodies of the invention have a number of uses. The antibodies may be used to purify vitamin D response element binding proteins from either recombinant or non-recombinant cells. The subject antibodies may be used to detect and/or quantify the presence of vitamin D response element binding proteins in tissue samples, e.g., from blood, skin, and the like. Quantitative measurements of vitamin D response element binding proteins may be used diagnostically for those diseases and physiological or genetic conditions that have been correlated with particular levels of vitamin D response element binding protein expression levels. The invention having been described above, may be better understood by referring to the following examples. The following examples are offered for the purpose of illustrating the invention and should not be interpreted as a limitation of the invention.

5.0. EXAMPLES

Examples generally useful for making and using the claimed invention can be found in the article Arbelle et al., "Inhibition of Vitamin D Receptor-Retinoid X Receptor-Vitamin D response Element Complex Formation by Nuclear Extracts of Vitamin D-Resistant New World Primate Cells" Endocrinology 137:786–789 (1996) which is incorporated herein by reference. This article is merely cited for purposes of guidance and any theories expressed in the article are merely theories and should not be construed as limitations of the invention described in the subject application.

5.1. Cell Culture

The B-lymphoblastoid cell line B95-8 and MLA-144 were obtained from the American Type Culture Collection (ATCC, Rockville, Md.). Both cell lines were maintained in RPMI-1640 medium (Irvine scientific Irvine, Calif.) routinely supplemented with 10% fetal calf serum (FCSI Gemini Bioproducts, Calabasas, Calif.), 100 ug/ml streptomycin, 2 mM L-glutamine (both from GIBCO-BRL, Grand Island, N.Y.) and in atmosphere of 95% air, 5% $CO_2$. In some experiments, confluent cultures were preincubated overnight in medium containing 100 nM 17β-estradiol, 25-hydroxyvitamin D3 (25-OHD3) and 1,25-dihydroxyvitamin D3 (1,25-$(OH)_2D_3$) prior to harvest and extract preparation.

5.2. Preparation of Cellular Extracts

B95-8 and MLA-144 cells were obtained from the ATCC (Rockville, Md.). Nuclear extracts were prepared as described by Zervitz and Akusjarvi (6) prior to or after overnight incubation in the presence of 100 nM 1,25-$(OH)_2D_3$ (Leo Pharmaceuticals, Ballerup, Denmark). Postnuclear extracts were prepared as previously described (5); crude extract was clarified by centrifugation at 100,000× g for 1 hour at 4° C. The 100,000× g supernatant, solubilized in ETD buffer (1 mM EDTA, 10 mM Tris-HCl, pH 7.4, 5 mM DTT, 1 mM PMSF) was diluted 1:1 with ETD (pH 8.0) buffer containing 0.20 M NaCl and pumped onto a 2.0 cm×2.5 cm BPS-DE column equilibrated in ETD-0.1 M NaCl, using a Pharmacia FPLC system (Uppsala, Sweden). Adsorbed proteins were eluted with a linear NaCl-containing gradient ranging from 0.1–2.0 M NaCl at a flow rate of 1.0 ml/min. Fractions containing protein with specific [$^3$H]25-$OHD_3$ binding activity (eluting between 0.7–1.0 M NaCl) were collected, pooled and tested by EMSA.

5.3. Electromobility Shift Assay (EMSA)

Transfected yeast (*S. cerevisiae*) extract enriched for the human VDR and for the human RXRα and anti-VDR antibody 9A7γ were prepared by standard methods (Arbelle et al., 1996, Endocrinology 137(2) :786–789). Anti-RXR antibody, 4RX-1D12, recognizing the α, β and γ forms of RXR was generously supplied by P. Chambon (Cedex, France). Synthetic oligonucleotides containing sequence of either the mouse osteopontin (opVDRE; GGTTCAcgaGGTTCA) (SEQ ID NO:1); or the human osteocalcin vitamin D response element (ocVDRE; GGGTGAacg GGGGCA) (SEQ ID NO:2) were prepared in the Molecular Biology Core Facility, Cedars-Sinai Research Institute. A double stranded oligonucleotide of comparable length representing the CTF/NF1 consensus sequence was purchased from Promega (Madison, Wis.). Single strand oligonucleotides were annealed with their complementary sequences and radiolabeled with $^{32}$P-γATP (DuPont NEN, Boston, Mass.) by T4 kinase (specific activity of $10^8$ cpm/mg DNA). Protein (8–18 μg) was incubated on ice with 50 fmol radiolabeled probe in the presence of 20 mM Hepes (pH 7.9), 0.1 M KCl, 5 mM $MgCl_2$, 1 μg d(I●C), and 10% glycerol for 15 min prior to electrophoresis on a 0.5× TBE-6% polyacrylamide gel. In some experiments nuclear extract was preincubated for 15 min on ice with either antibodies or excess unlabeled double stranded DNA prior to incubation with probe. Gels were dried for 1 h at 80° C. and exposed to Kodak X-OMAT AR film for 1 to 18 h at 70° C. with an enhancing screen or for 1 h to 3 d at 23° C.

5.4. Nuclear and Postnuclear Extracts of NWP Cells Contain a Protein Which Binds to VDRE Given the facts that: 1) nuclear extracts of B95-8 cells contain normal amounts of normally functioning VDR when assessed in vitro; and 2) the 1,25-$(OH)_2D_3$ liganded VDR—RXR heterodimer has been shown to exhibit the highest affinity for the VDRE, it was anticipated that similarly-prepared nuclear extracts from NWP and OWP cells would interact similarly with a synthetic VDRE. As expected a specific band representing the heterodimerized VDR—RXR bound to the radiolabeled mouse opVDRE was detected when either yeast extracts or 1,25-$(OH)_2D_3$-treated OWP cell nuclear extracts were used as a source of VDR and RXR. No bands containing VDR—RXR were identified when nuclear extracts from the vitamin D-resistant B95-8 cell line were used under the same conditions. Neither pre-exposure of the vitamin D-resistant cells overnight to 100 nM 1,25-$(OH)_2D_3$ nor direct exposure of the nuclear extract to 100 nM 1,25-$(OH)_2D_3$ immediately prior to incubation with the opVDRE probe elicited a specific VDR—RXR—VDRE band in the EMSA. Results identical to those with the opVDRE were obtained with the ocVDRE as probe.

Although a band containing the VDR—RXR heterodimer could not be seen upon incubation of the vitamin D-resistant B95-8 cell nuclear extract with the radiolabeled opVDRE, two other bands were detected. The slower migrating nuclear protein-VDRE complex (NWP-NP) was competed off the probe by a 20–100-fold molar excess of unlabeled opVDRE. A 100-fold excess of oligonucleotide containing a direct repeat of either AGGTCA or GGTTCA with a 3 base pair spacer and the consensus estrogen response element (ERE: AGGTCAcagTGACCT) (SEQ ID NO:3) were all capable of decreasing the intensity of the NWP-NP band by 64%, 61%, and 57%, respectively. A 100-fold excess of oligonucleotide containing the glucocorticoid response element (GRE) (AGAACAtccTGTTCT) (SEQ ID NO:4) or of the irrelevant sequence CTFNF1 did not effect binding. The intensity of the faster migrating complex was not affected by inclusion of either specific or nonspecific unlabeled oligomer in the reaction. Neither of these bands were present when the wild type MLA-144 nuclear extract was employed in the gel shift analysis. Furthermore, neither the intensity nor the position of either of these bands changed subsequent to addition of anti-VDR or anti-RXR antibodies to the binding reaction. Taken together, these results suggest that a protein(s), other than the VDR—RXR heterodimer, is present in the nuclear extract of vitamin D-resistant NWP cells and is capable of binding to the VDRE and to the ERE with high affinity. These data further indicated that at least one factor present in the same nuclear extract was capable of inhibiting binding of the VDR—RXR heterodimer to the VDRE.

To test whether a factor present in the nuclear extract of vitamin D-resistant NWP cells was inhibiting VDR—RXR—VDRE complex formation, a mixing experiment was performed. Vitamin D-resistant B95-8 cell nuclear extract containing a putative "inhibiting factor" was incubated with a mixture of human VDR and RXRα prior to incubation with radiolabeled opVDRE in gel shift analysis. Formation of the VDR—RXR—VDRE complex was inhibited even in the presence of the large amount of VDR and RXR protein present in the yeast-expressed extracts. This inhibitory effect was abolished by diluting the B95-8 nuclear extract 1:10, or by heat-treating the extract prior to mixing with VDR—RXR. No such inhibitory activity was demonstrated when equal amounts of: 1) the post nuclear extract of vitamin D-resistant cells; 2) the postnuclear extract of vitamin D-resistant cells enriched >20-fold in IDBP by purification over an anion exchange column; or 3) the nuclear extract from wild type OWP cells were used in place of the nuclear extract from vitamin D-resistant cells. These results suggest that the factor enriched in NWP cells is heat labile, confined largely to the nuclear compartment, and functionally distinct from the IDBP which is concentrated in the cytoplasm of the NWP cell.

5.5. Affinity Purification of the NWP VDRE—BP

The DNA affinity column was prepared essentially as described by Kadondaga and Tijan. Two gel-purified oligodeoxynucleotides containing the consensus VDRE were synthesized. Approximately 200 μg of each oligonucleotide was annealed, 5'-phosphorylated with [gamma-$^{32}$P] ATP to ascertain coupling efficiency, and ligated. The resultant DNA oligomers were then coupled to cyanogen bromide (CNBr)-activated Sepharose 4B (Pharmacia, Piscataway, N.J.). After blocking the excess remaining active groups with ethanolamine, the DNA-coupled resin was placed in a 2 ml poly-prep column (BIO-Rad, Hercules, Calif.) for chromatography. The column was equilibrated in elution buffer (25 mM Hepes [pH 7.6], 12.5 mM MgCl$_2$, 1 mM DTT, 20% glycerol, and 0.1% nonidet P-40) containing 0.1 M KCl. The NWP cell extract (13–20 mg prepared as described) above was solubilized in the elution buffer containing nonspecific competitor poly dIdC (4 mg/ml) and added to the column at a flow rate of about (12 ml/hour). Protein was then eluted from the column in using a gradient of elution buffer containing about 0.1–1.0 M KCl. Fractions (2 ml) from each column eluate was concentrated and desalted through a Microcon-30 filter and VDRE binding capacity assessed by EMSA. An aliquot of each fraction was used to determine total protein concentration. The constituent proteins in each fraction were resolved on a 10% SDS-PAGE and identified by silver staining.

Several fractions eluted from the affinity column were enriched for a protein that interacted with the VDRE in EMSA. The specific activity of this VDRE—BP activity was increased by over 10,000 fold (as measured by the ability to compete with VDR—RXR for binding to the VDRE). Subsequent studies have provided greater than 20,000-fold purification of the VDRE—BP activity over that present in the material loaded onto the affinity column. SDS-PAGE of the relevant fractions from DNA affinity chromatography disclosed the presence of three bands with relative mobilities corresponding to proteins of about 45 kDa, 65 kDa, and 110 kDa. The 45 and 65 kDa bands are presumed to be either subunits or degradation products of the 110 kDa protein. EMSA using these protein(s) was not affected by exposure to vitamin D receptor antibodies.

5.6. Identification and Cloning of Polynucleotides Encoding VDRE—BP

The purified VDRE—BP described above was subject to proteolytic digest and the purified fragments were subject to amino acid sequence analysis. Two amino acid sequences (SRSGGGGGGGIGSGGSLR (SEQ ID NO:5) and FYLP*EI*DYGQDEEAVK) (SEQ ID NO:6) have been identified that may be used as the basis for designing degenerate oligonucleotide probes (for hybridization screening), or primers (for PCR screening) useful for screening cDNA libraries. The cDNA clones identified by oligonucleotide screening methods are sequenced to determine whether they encode a protein corresponding to the known amino acid sequence derived from the VDRE—BP. Subsequently, such clones are used as probes for the identification and isolation of full-length genes, preferably cDNAs, encoding VDRE—BP genes from any of a variety of animal species.

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described makes for carrying out the invention which are obvious to those skilled in the field of organic chemistry or related fields are intended to be within the scope of the following claims.

What is claimed is:

1. A vitamin D response element binding protein isolated from a mammal, or a functional fragment thereof, wherein said protein is distinct from a vitamin D receptor, wherein said protein or fragment binds to a vitamin D response element, wherein said protein or fragment inhibits binding of the vitamin D receptor to a vitamin D response element, and wherein said protein has a molecular weight selected from about 110 kDa, about 65 kDa, or about 45 kDa as determined by sodium dodecyl sulfate polyacrylamide gel electrophoresis.

2. A vitamin D response element binding protein according to claim 1, wherein the mammal is a primate.

3. A vitamin D response element binding protein according to claim 2, wherein the primate is human.

4. A vitamin D response element binding protein according to claim 2, wherein the primate is *Callithrix jacchus.*

5. A vitamin D response element binding protein according to claim 1, wherein said protein has a molecular weight of about 110 kDa as determined by sodium dodecyl sulfate polyacrylamide gel electrophoresis.

6. A functional fragment according to claim 1, wherein said functional fragment has a molecular weight of about 65 kDa as determined by sodium dodecyl sulfate polyacrylamide gel electrophoresis.

7. A functional fragment according to claim 1, wherein said functional fragment has a molecular weight of about 45 kDa as determined by sodium dodecyl sulfate polyacrylamide gel electrophoresis.

8. A vitamin D response element binding protein or fragment according to claim 1, wherein said protein or fragment comprises at least one amino acid sequence selected from the group consisting of SEQ ID NO:5 and SEQ ID NO:6.

\* \* \* \* \*